United States Patent
Atashbar et al.

(10) Patent No.: US 10,966,622 B2
(45) Date of Patent: Apr. 6, 2021

(54) PRINTED ECG ELECTRODE AND METHOD

(71) Applicant: The Board of Trustees of Western Michigan University, Kalamazoo, MI (US)

(72) Inventors: Massood Zandi Atashbar, Portage, MI (US); Amer Abdulmahdi Chlaihawi, Kalamazoo, MI (US); Binu Baby Narakathu, Portage, MI (US); Ali Eshkeiti, Kalamazoo, MI (US)

(73) Assignee: The Board of Trustees of Western Michigan University, Kalamazoo, MI (US)

( * ) Notice: Subject to any disclaimer, the term of this patent is extended or adjusted under 35 U.S.C. 154(b) by 590 days.

(21) Appl. No.: 15/591,856

(22) Filed: May 10, 2017

(65) Prior Publication Data
US 2017/0332928 A1    Nov. 23, 2017

Related U.S. Application Data

(60) Provisional application No. 62/339,397, filed on May 20, 2016.

(51) Int. Cl.
*A61B 5/0408* (2006.01)

(52) U.S. Cl.
CPC .... *A61B 5/0408* (2013.01); *A61B 2562/0209* (2013.01); *A61B 2562/0285* (2013.01); *A61B 2562/125* (2013.01); *A61B 2562/166* (2013.01)

(58) Field of Classification Search
CPC ............ A61B 5/0408; A61B 2562/125; A61B 2562/0215; A61B 2562/046; A61B 5/04; A61B 5/6804; A61B 5/0402
USPC .......................... 600/372, 382, 395, 508–509
See application file for complete search history.

(56) References Cited

U.S. PATENT DOCUMENTS

| | | | |
|---|---|---|---|
| 6,815,008 B2 | 11/2004 | Ichikawa et al. | |
| 8,304,027 B2 | 11/2012 | Yokoyama et al. | |
| 8,608,941 B2 | 12/2013 | Taranekar et al. | |
| 8,608,984 B1 | 12/2013 | Taranekar et al. | |
| 9,282,893 B2 | 3/2016 | Longinotti-Buitoni et al. | |
| 2003/0088239 A1* | 5/2003 | Takaki | C09J 9/02 606/1 |

(Continued)

FOREIGN PATENT DOCUMENTS

| | | |
|---|---|---|
| EP | 3001184 A1 | 3/2016 |
| WO | 2015157272 A1 | 10/2015 |
| WO | 2016054484 A1 | 4/2016 |

OTHER PUBLICATIONS

Liu et al. "Patterning conductive PDMS nanocomposite in an elastomer using microcontact printing" J. Micromech. Microeng. 19 (Jun. 2009) (Year: 2009).*

(Continued)

*Primary Examiner* — Joseph A Stoklosa
*Assistant Examiner* — Brian M Antiskay
(74) *Attorney, Agent, or Firm* — Price Heneveld LLP

(57) ABSTRACT

A flexible dry electrode comprises a multi-walled carbon nanotube (MWCNT)/polydimethylsiloxane (PDMS) composite. The flexible dry electrode may be utilized for monitoring electrocardiogram (ECG) signals. The dry ECG electrode may be fabricated by screenprinting silver (Ag) ink on flexible polyethylene terephthalate (PET) substrate, followed by bar coating of a MWCNT/PDMS composite.

12 Claims, 10 Drawing Sheets

(56) References Cited

U.S. PATENT DOCUMENTS

| | | | |
|---|---|---|---|
| 2008/0275327 | A1 | 11/2008 | Faarbaek et al. |
| 2009/0318793 | A1* | 12/2009 | Datta .................... A61B 5/062 600/391 |
| 2010/0016702 | A1* | 1/2010 | Greene ................ A61B 5/0408 600/391 |
| 2010/0231672 | A1 | 9/2010 | Joyce et al. |
| 2012/0111599 | A1 | 5/2012 | Roberson et al. |
| 2013/0303873 | A1* | 11/2013 | Voros ................ A61B 5/04001 600/377 |
| 2015/0367122 | A1* | 12/2015 | Morshed .............. A61B 5/0408 600/372 |
| 2016/0007874 | A1* | 1/2016 | Ma ....................... A61B 5/6868 600/374 |
| 2016/0033343 | A1* | 2/2016 | Park ........................ G01L 1/205 73/862.046 |
| 2016/0089045 | A1* | 3/2016 | Sadeghian-Motahar .................... A61B 5/04 600/386 |
| 2016/0106333 | A1 | 4/2016 | Kang et al. |
| 2017/0172446 | A1* | 6/2017 | Kuzum .............. G01N 33/5438 |
| 2017/0213648 | A1 | 7/2017 | Joyce et al. |

OTHER PUBLICATIONS

Tai et al. "Flexible pressure sensing film based on ultrasensitive SWCNT/PDMS spheres for monitoring human pulse signals". J. Mater. Chem. B, 2015, 3, 5436. (Year: 2015).*

Liu et al. "A novel method of fabricating carbon nanotubes-polydimethylsiloxane composite electrode for electrocardiography" Aug. 2015 (Year: 2015).*

U.S. Appl. No. 15/595,243, filed May 15, 2017, 16 pages.

Office Action, Application No. 2,930,837, dated May 26, 2017, 5 pages.

Lee et al., "Wearable heart electrical activity monitoring using circular ring electrode," Proc. World Congress Med. Phys. Biomed. Eng., vol. 14, pp. 4088-4091, 2006, 4 pages.

D. Mozaffarian et al., "Executive summary: Heart disease and stroke statistics—2015 Update," J. Am. Heart Assoc., vol. 4, pp. 434-442, 2015, 9 pages.

Baek et al., "Flexible polymeric dry electrodes for the long-term monitoring of ECG," Sens. Act. A, vol. 143, pp. 123-429, Nov. 24, 2007, 7 pages.

P. Salvo et al., "A 3D printed dry electrode for ECG/EEG recording," Sens.Act. A, vol. 174, pp. 96-102, Dec. 17, 2011.

T. Inoh et al., "Nanofiber web textile dry electrodes for long-term biopotential recording," IEEE Trans. Biomed. Circuits Syst., vol. 7(2), pp. 204-211, Apr. 2013, 8 pages.

A. Myers et al., "Wearable silver nanowire dry electrodes for electrophysiological sensing," Royal Society of Chemistry , vol. 5(15), pp. 11627-11632, 2015, 6 pages.

C. O'Mahonu, "Microneedle-based electrodes with integrated through-silicon via for biopotential recording," Sens. Act. A, vol. 186, pp. 130-136, May 22, 2012, 7 pages.

B. Narakathu et al., "Novel fully screen printed flexible electrochemical sensor for the investigation of electron transfer between thiol functionalized viologen and gold clusters," Sens. Act. B, vol. 176, pp. 768-774, Oct. 22, 2012, 7 pages.

H. Jung et al., "CNT/PDMS composite flexible dry electrodes for long-term ECG monitoring," Proc. IEEE Trans. Biomed. Eng., vol. 59 (5), pp. 1472-1479, May 2012, 8 pages.

K. Hoffmann and R. Ruff, "Flexible dry surface-electrodes for ECG long-term monitoring," Proc. IEEE Conf. Eng. Med. Biol. Soc. (EMBC), pp. 5739-5742, Aug. 23, 2007, 4 pages.

* cited by examiner

PRINTED ECG ELECTRODE AND METHOD

CROSS REFERENCE TO RELATED APPLICATION

This application claims the benefit of U.S. Provisional Application No. 62/339,397 filed on May 20, 2016, entitled, "PRINTED ECG ELECTRODE AND METHOD," the entire contents of which are incorporated herein by reference.

BACKGROUND OF THE INVENTION

Cardiovascular disease (CVD) is a major cause of death. Electrocardiogram is one of the most frequently used techniques for monitoring the heart's electrical signals to investigate and diagnose symptoms related to heart problems. Even though wet Ag/AgCl electrodes are widely used for monitoring ECG signals and have good signal stability, it has drawbacks such as requiring skin preparation and using conductive gels that often causes irritation or allergies of the skin. In addition, motion artifacts reduce the performance of wet electrodes due to relative motion of electrodes with the body as well as drying of the conductive gel.

Several research groups have reported on the use of dry electrodes such as nanofiber web textile dry electrodes, silver nanowire dry electrode, conductive fabric textile dry electrode and circular ring electrode for ECG measurements. These dry electrodes can be applied for long-term ECG monitoring and used multiple times without the use of conductive gel. However, the fabrication of these dry electrodes may require the use of metallic electrodes as well as metal or rigid substrates, which are not conformal enough and may cause damage to the skin. Several studies have reported on the development of conductive polymers by coating, dispersing or encapsulating metallic electrode surfaces with materials such as polyvinylidene fluoride (PVDF), polydimethylsiloxane (PDMS) and conductive polymer foam. In addition, traditional printing processes such as gravure, screen and inkjet have also been employed for the development of low cost, lightweight, biocompatible and flexible electronic devices.

BRIEF SUMMARY OF THE INVENTION

A flexible dry electrode comprises a multi-walled carbon nanotube (MWCNT)/polydimethylsiloxane (PDMS) composite. The flexible dry electrode may be utilized for monitoring electrocardiogram (ECG) signals. The dry ECG electrode may be fabricated by screenprinting silver (Ag) ink on flexible polyethylene terephthalate (PET) substrate, followed by bar coating of a MWCNT/PDMS composite.

Another aspect of the present disclosure is a method of fabricating a dry ECG electrode. The method includes printing conductive ink such as silver onto a polymer substrate to form a conductive layer. At least a portion of the conductive layer is coated with a composite material comprising carbon nanoparticles disposed in a polymer matrix material. The carbon nanoparticles may comprise multiwall carbon nanotubes (MWCNTs), and the polymer matrix may comprise polydimethylsiloxane.

These and other features, advantages, and objects of the present invention will be further understood and appreciated by those skilled in the art by reference to the following specification, claims, and appended drawings.

DETAILED DESCRIPTION

Figure 1A:
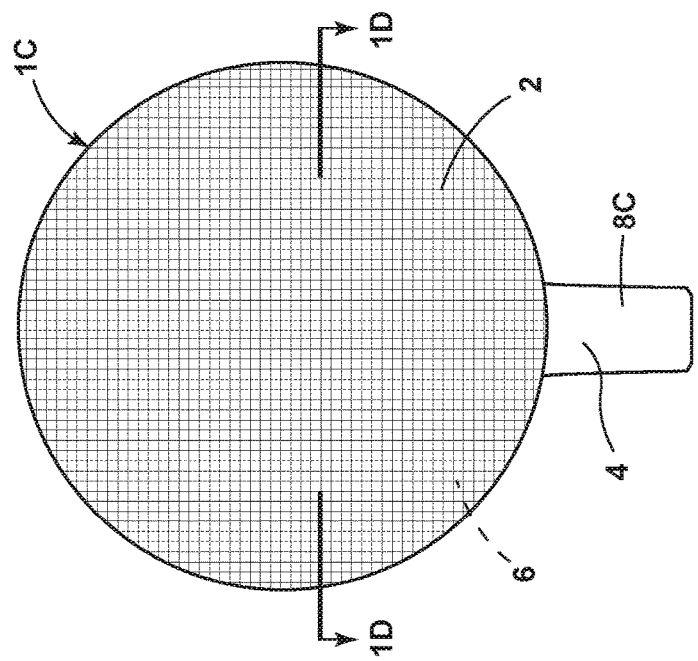
FIGS. 1A, 1B, and 1C show screen printed dry ECG electrodes having radii of 8 mm, 12 mm, and 16 mm, respectively.
Figure 1B:
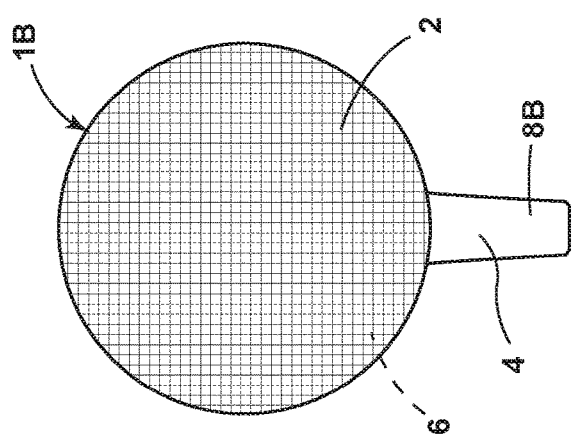
Figure 1C:
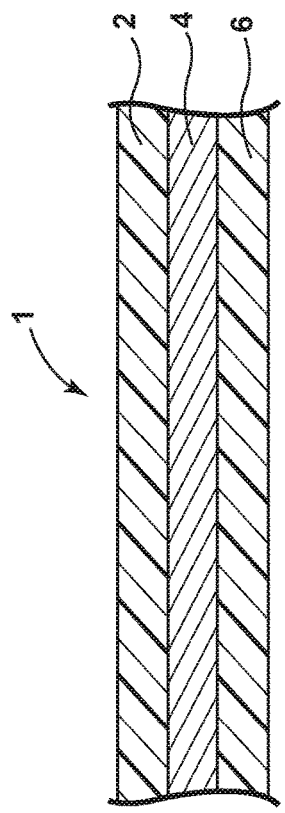

For purposes of description herein, the terms "upper," "lower," "right," "left," "rear," "front," "vertical," "horizontal," and derivatives thereof shall relate to the disclosure as oriented in FIG. 1. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As discussed in more detail below, a printed, flexible dry ECG electrode 1 (FIGS. 1A-1C) according to the present disclosure comprises a multi-walled carbon nanotube (MWCNT)/polydimethylsiloxane (PDMS) composite layer 2 (FIG. 1D) that is deposited onto a conductive layer 4 utilizing a bar coating process. The conductive layer 4 may be formed by screen printing a suitable conductive ink such as silver (Ag) onto a flexible substrate 6. Flexible substrate 6 may comprise a suitable polymer material such as a polyethylene terephthalate (PET). In use, the composite layer 2 is placed in contact with a patient's body (e.g. skin), and electrical signals produced by the patient's body (e.g. ECG signals) may be measured and processed utilizing known ECG equipment/instruments or other devices.

As also discussed below, the performance of ECG electrodes fabricated utilizing a process according to the present disclosure were investigated by measuring ECG signals using printed dry electrodes 1A, 1B, 1C (FIGS. 1A, 1B, 1C) with radii varying from 8 mm to 16 mm, respectively. The electrodes may be circular, oval, or other suitable shape. The results were compared with a traditional wet Ag/AgCl ECG electrode (T716). It was observed that the dry ECG electrode 1C with the largest area (FIG. 1C), demonstrated better performance, in terms of signal intensity and correlation, when compared to the traditional wet ECG electrode. The responses of the dry ECG electrodes 1A, 1B, 1C are analyzed in more detail below.

The flexible dry ECG electrode 1 may be printed with conductive ink (e.g. silver) on a thin polymer substrate and bar coated with PDMS that is doped with multi-walled carbon nanotubes (MWCNT). The PDMS sticks to human skin well, and the MWCNT provides conductance of ECG signals to the electrode. The bar coating and screen printing may be accomplished utilizing known processes.

EXAMPLE

The following is an example of a specific process utilized to fabricate an ECG electrode. It will be understood that the present invention is not limited to this example.

A. Chemicals and Materials

PDMS, which was used to prepare the conductive polymer, was purchased as a two-part heat curable silicone elastomer kit (SYLGARD® 184) from Dow Corning. High purity MWCNTs (about 95%) were purchased from US Researchers Nanomaterial, Inc. The MWCNTs have an outer diameter of about 20-30 nm, an inner diameter of 5-10 nm and electrical conductivity that is greater than about 100 S/cm. Ag ink (Electrodag 479SS, Henkel) was used for metallization of the dry flexible ECG electrode. Flexible PET (Melinex® ST506 PET, available from DuPont Teijin Films) was used as the substrate. Toluene solvent (available from Sigma Aldrich Chemical Company) was used to facilitate mixing and dispersion of both the PDMS and MWCNTs. Wet Ag/AgCl ECG electrode (T716) was purchased from Bio-Protech Inc.

B. Conductive MWCNT/PDMS Composite Preparation

The composite polymer was developed by mixing conductive MWCNTs with non-conductive PDMS. In order to reduce the agglomeration due to Van der Waals forces and achieve a good dispersion, magnetic stirring was used in all steps. The SYLGARD® 184 comprised a polymer base resin (Part-A) and a curing agent (Part-B). First, a MWCNT/Toluene dispersion was prepared by dispersing MWCNT in toluene (1:15 w/w) and a PDMS Part-A/Toluene dispersion was prepared by dispersing PDMS Part-A in toluene (1:3 w/w). Both solutions were magnetically stirred for about 1 hour at room temperature. Next, the MWCNT/Toluene dispersion was added to the PDMS Part-A/Toluene dispersion and mixed for about 1 hour at room temperature using magnetic stirring. After this, the mixture was again magnetically stirred for about 3 hours on a hot plate at 70° C. to form a homogeneous MWCNT/PDMS composite with about 8% MWCNT by weight. The solution was then sonicated for about 30 minutes. Finally, PDMS Part-B was added to the solution (1:10 w/w) and magnetically stirred for about 30 minutes at room temperature.

C. Dry ECG Electrode Fabrication

Figure 1D:
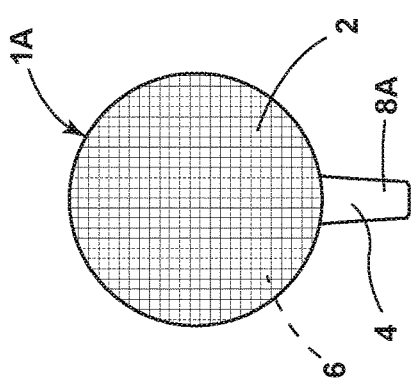
FIG. 1D is a schematic cross-sectional view of the ECG electrode of FIG. 1C.

An HMI MSP-485 high precision screen printer was used to print the Ag ink on the flexible PET substrate 6 (FIG. 1D). A 325 stainless steel mesh count screen (Microscreen®) with 28 μm wire diameter, 22.5° angle and 12.7 μm thick MS-22 emulsions was used. The printed Ag (e.g. layer 4, FIG. 1D) was cured in a VWR oven at about 120 °C for about 20 minutes. The prepared MWCNT/PDMS composite was then bar coated on the printed Ag layer 4 to form composite layer 2. Electrodes 1A, 1B, and 16 (FIGS. 1A, 1B, 1C, respectively) were formed with radii of about 8 mm, about 12 mm, and about 16 mm, respectively. The electrodes 1A, 1B, and 1C include leads 8A, 8B, 8C, respectively. Electrodes 8A, 8B, and 8C may comprise a bare portion of conductive layer 4 disposed on flexible substrate 6 that is not coated with composite layer 2. Finally, the ECG electrodes 1A, 1B, and 1C were again cured in a VWR oven at about 120° C. for 20 minutes to form the dry ECG electrodes 1A, 1B, 1C, with three different radii of about 8 mm (1A), about 12 mm (1B) and about 16 mm (1C).

D. Experiment Setup

Figure 2:
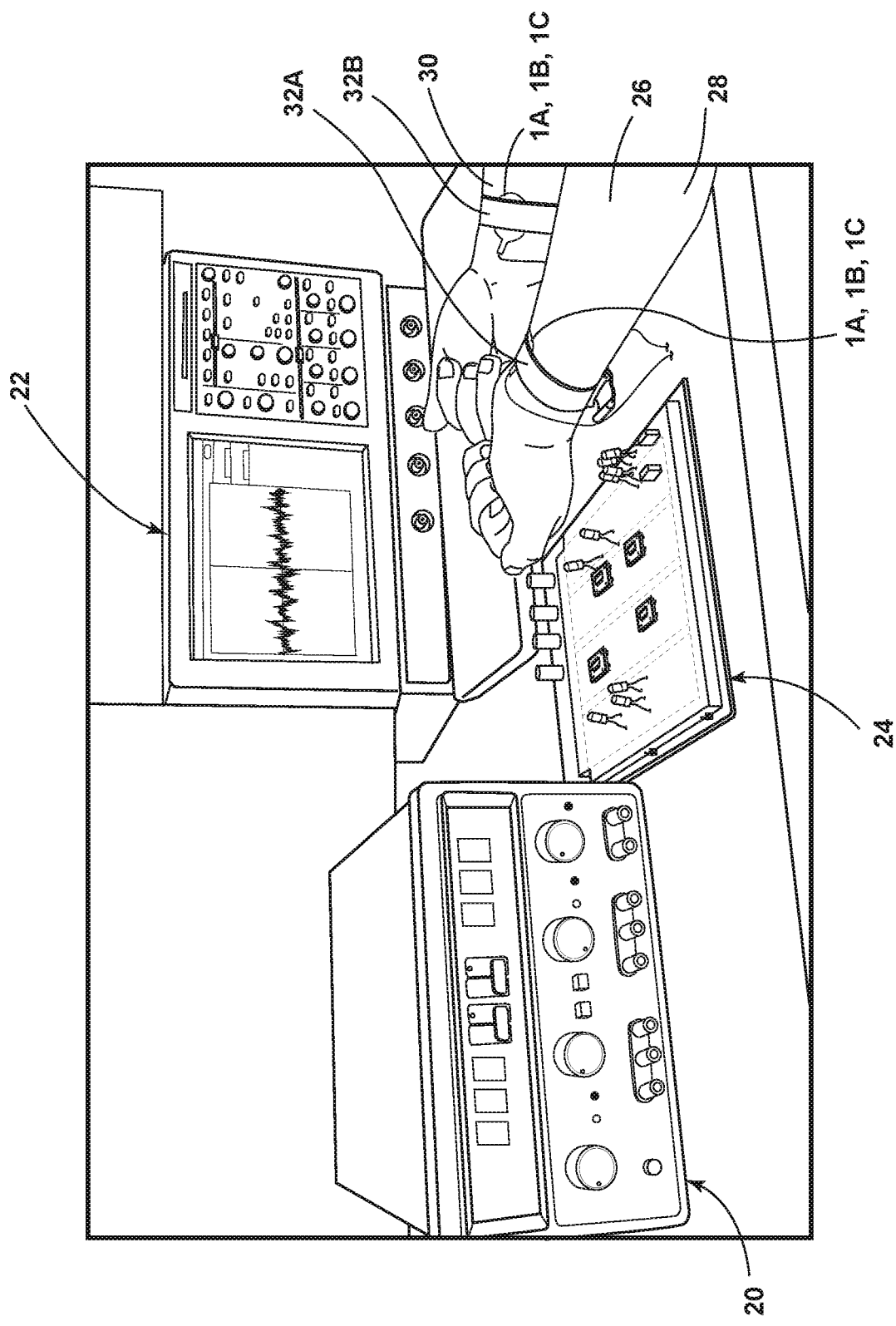
FIG. 2 is a perspective view of an ECG electrode test setup.

The performance of the fabricated dry ECG electrodes 1A, 1B, and 1C was investigated by monitoring ECG signals and comparing it against the response of a wet Ag/AgCl electrode. The experiment setup is shown in FIG. 2. It includes a power supply 20 (Tektronix, PS280 DC power supply), digital oscilloscope 22 (Tektronix, TDS510B Digital Phosphor Oscilloscope), printed dry ECG electrodes 1A, 1B, 1C, and an ECG data acquisition electronic circuit 24. All measurements were conducted at room temperature. Three dry electrodes (1A or 1B or 1C), with similar radius, were placed on the body 26 of a healthy volunteer at three positions: left forearm 28, right forearm 30 and right leg (not shown), without shaving the hair and with no skin preparation. The ECG electrodes 1A, 1B, 1C were retained via straps 32A, 32B with the composite layer 2 in contact with the patient's skin. No conductive (wet) gel or other conductive material was positioned between the composite layer 2 and patient's skin. The electrodes 1A, 1B, 1C were connected to the digital oscilloscope 22 for visualizing and recording the ECG signals. The ECG data acquisition electronic circuit 24 of this example includes a front-end amplifier circuit, instrumentation amplifier, a driven right leg (DRL) circuit, and an active filter. The front-end amplifier circuit contains a buffer amplifier to ensure high input impedance, and an AC coupler. The instrumentation amplifier is an Analog Devices INA 2128 chip with input impedance of 10 GΩ. The DRL circuit was used to reduce the common mode voltage in the biopotential amplifiers. The active filter consists of a notch filter, used to reduce 60 Hz base line interference, a Sallen Key low pass filter, with a cut-off frequency 150 Hz, and high pass filter, with cut-off frequency of 0.05 Hz.

Figure 3:
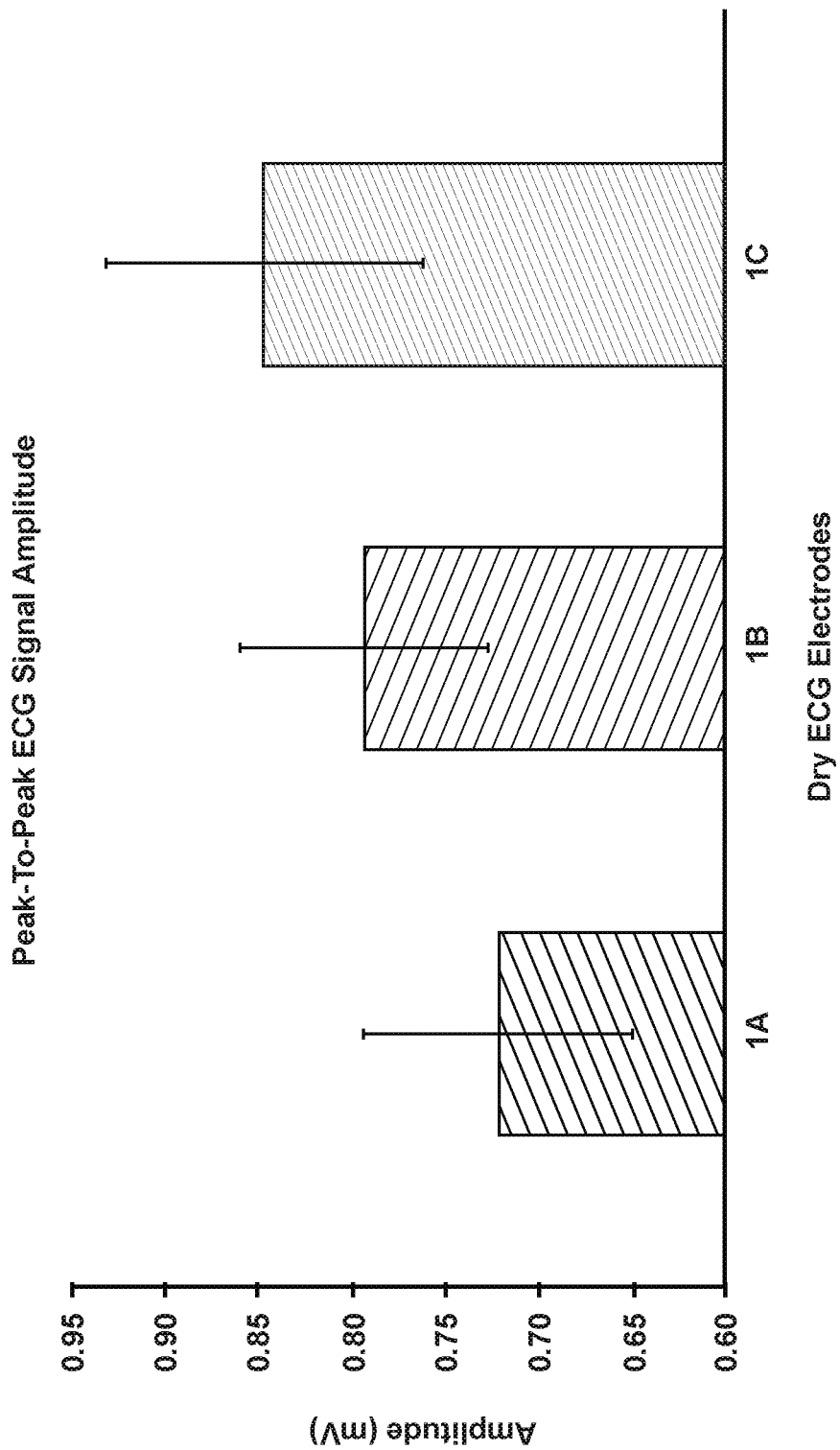
FIG. 3 is a graph showing ECG signal intensity for three different dry electrodes.

The performance of the ECG signal measurements was recorded in both the relaxed sitting position and while the body is in motion. It is known that the electrode-skin impedance is dependent on the electrode contact area on the skin. Hence, initially, the influence of the dry ECG electrodes 1A, 1B, 1C area on the ECG signal intensity was analyzed, in the relaxed position. It was observed that the peak-to-peak amplitude of the ECG signal was directly proportional to the area of the dry electrodes, with a maximum intensity for electrode 1C (FIG. 3). These results demonstrated that a better electrode performance is achieved by using the electrode (1C), which has a bigger electrode-skin interface area, for monitoring ECG signals.

Figure 4A:
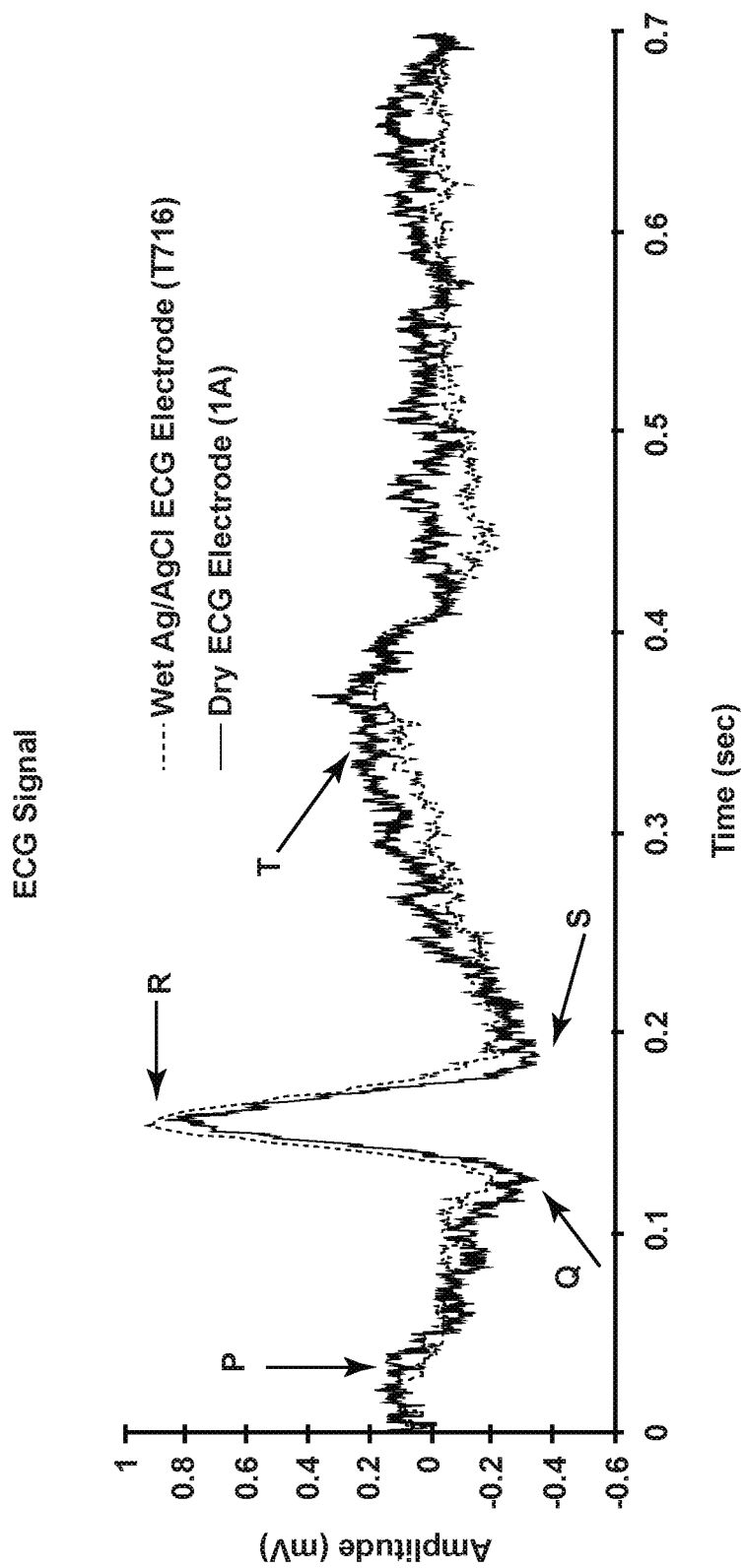
FIG. 4A is a graph showing the correlation between traditional wet Ag/AgCL electrode and printed dry ECG electrode for a first electrode.
Figure 4B:
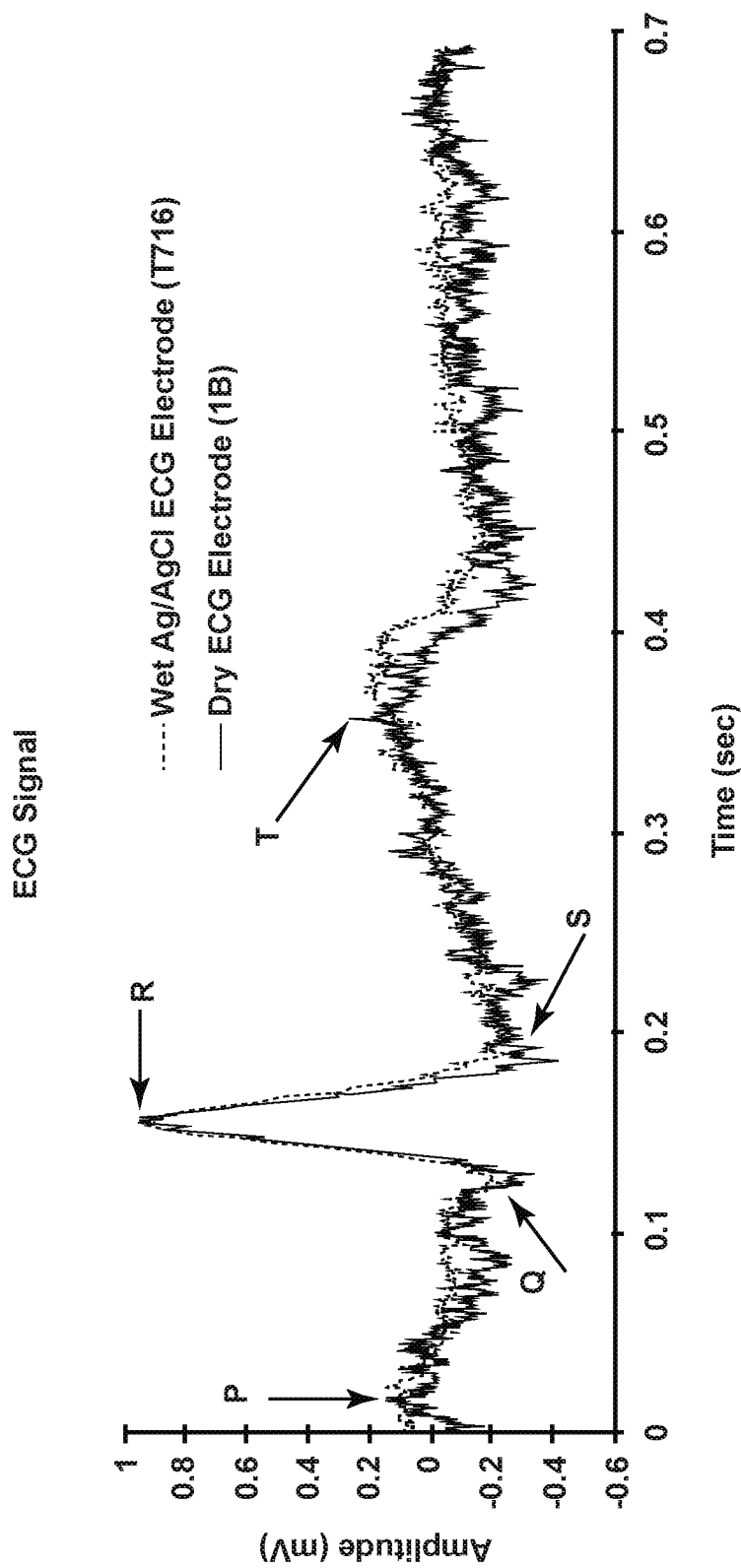
FIG. 4B is a graph showing the correlation between traditional wet Ag/AgCL electrode and printed dry ECG electrode for a second electrode.
Figure 4C:
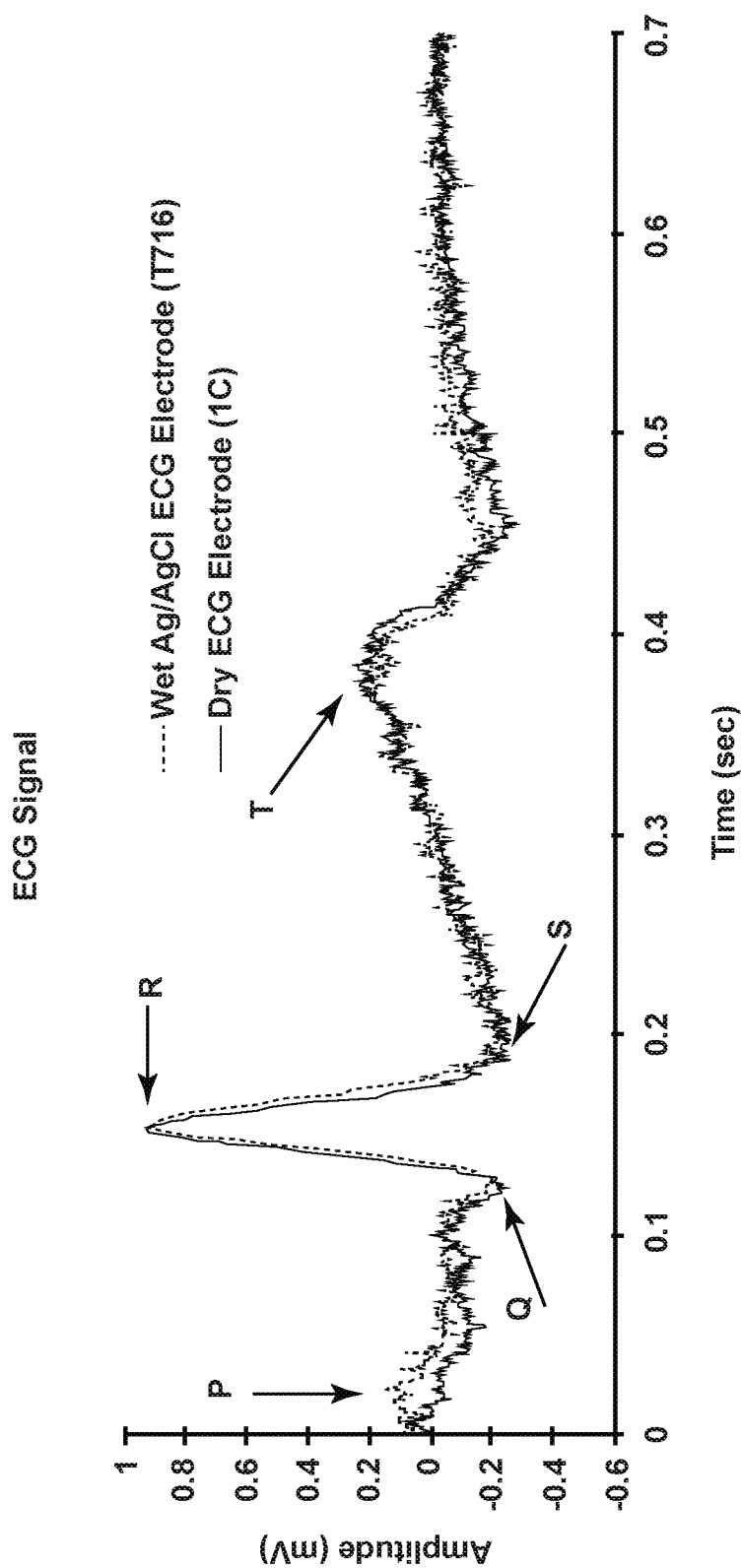
FIG. 4C is a graph showing the correlation between traditional wet Ag/AgCL electrode and printed dry ECG electrode for a third electrode.
Figure 5A:
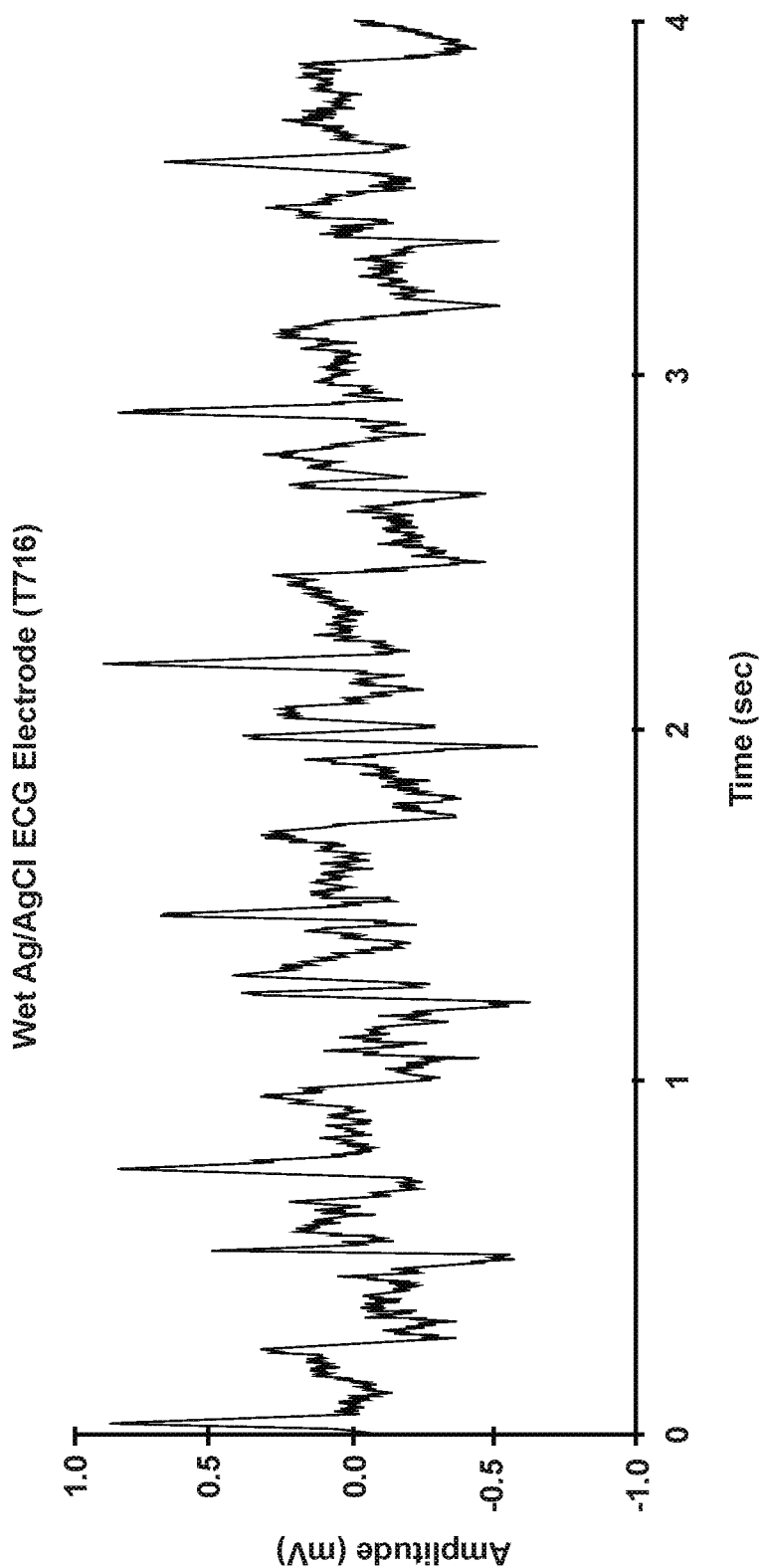
FIG. 5A shows ECG signal measurements for a wet Ag/AgCL electrode while the body is in motion.
Figure 5B:
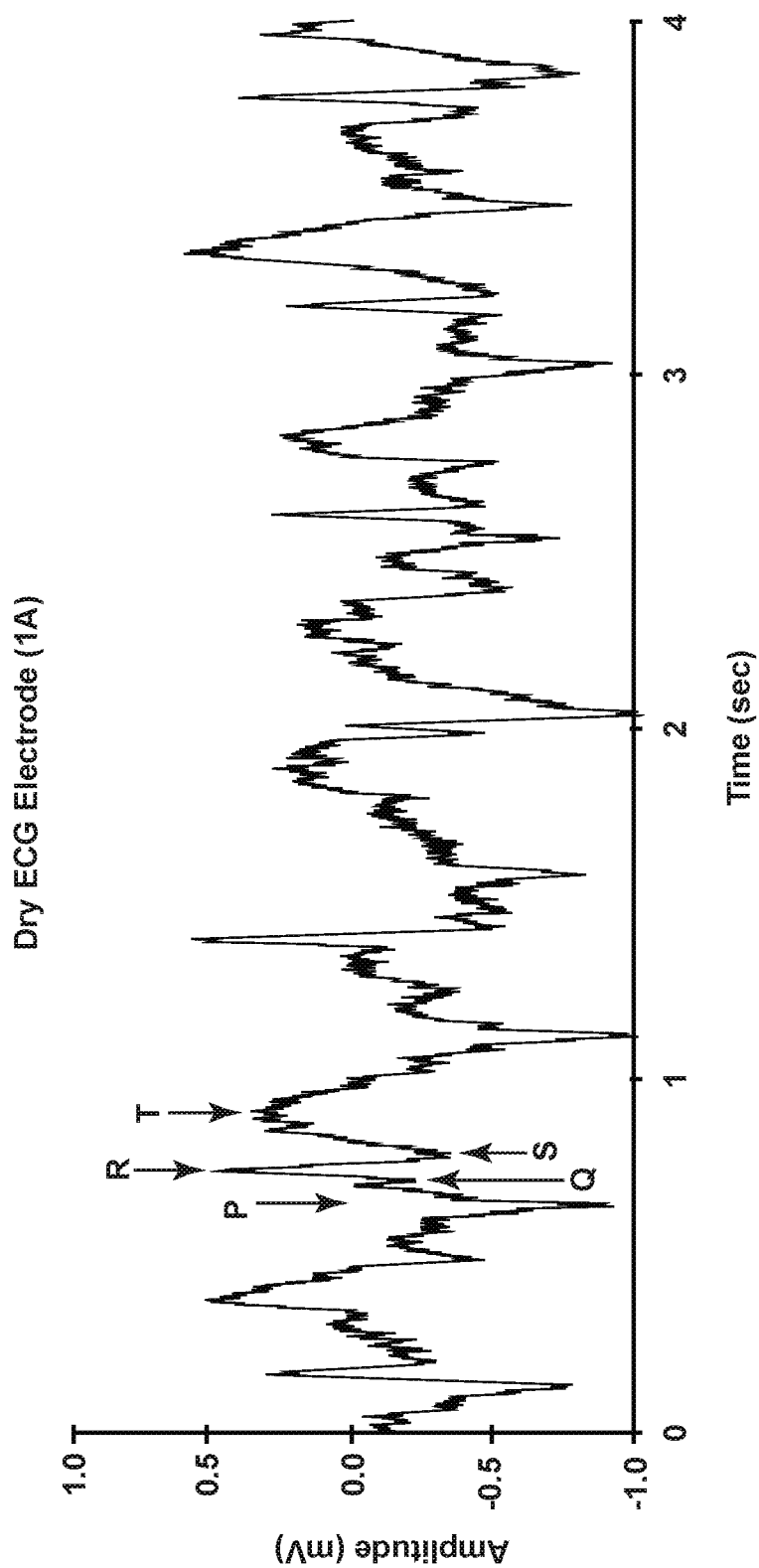
FIG. 5B shows ECG signal measurements for a dry first electrode while the body is in motion.
Figure 5C:
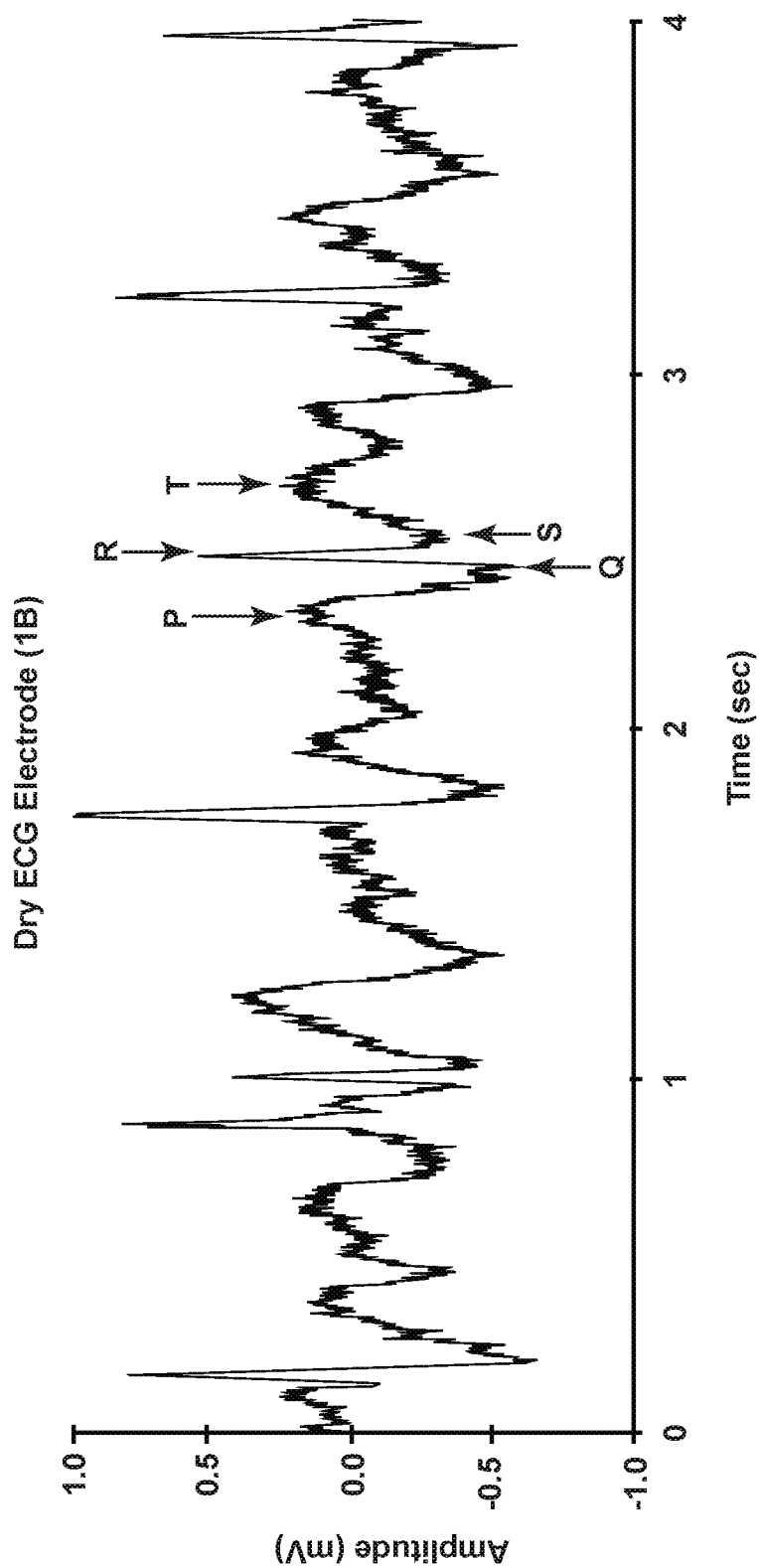
FIG. 5C shows ECG signal measurements for a dry second electrode while the body is in motion.
Figure 5D:
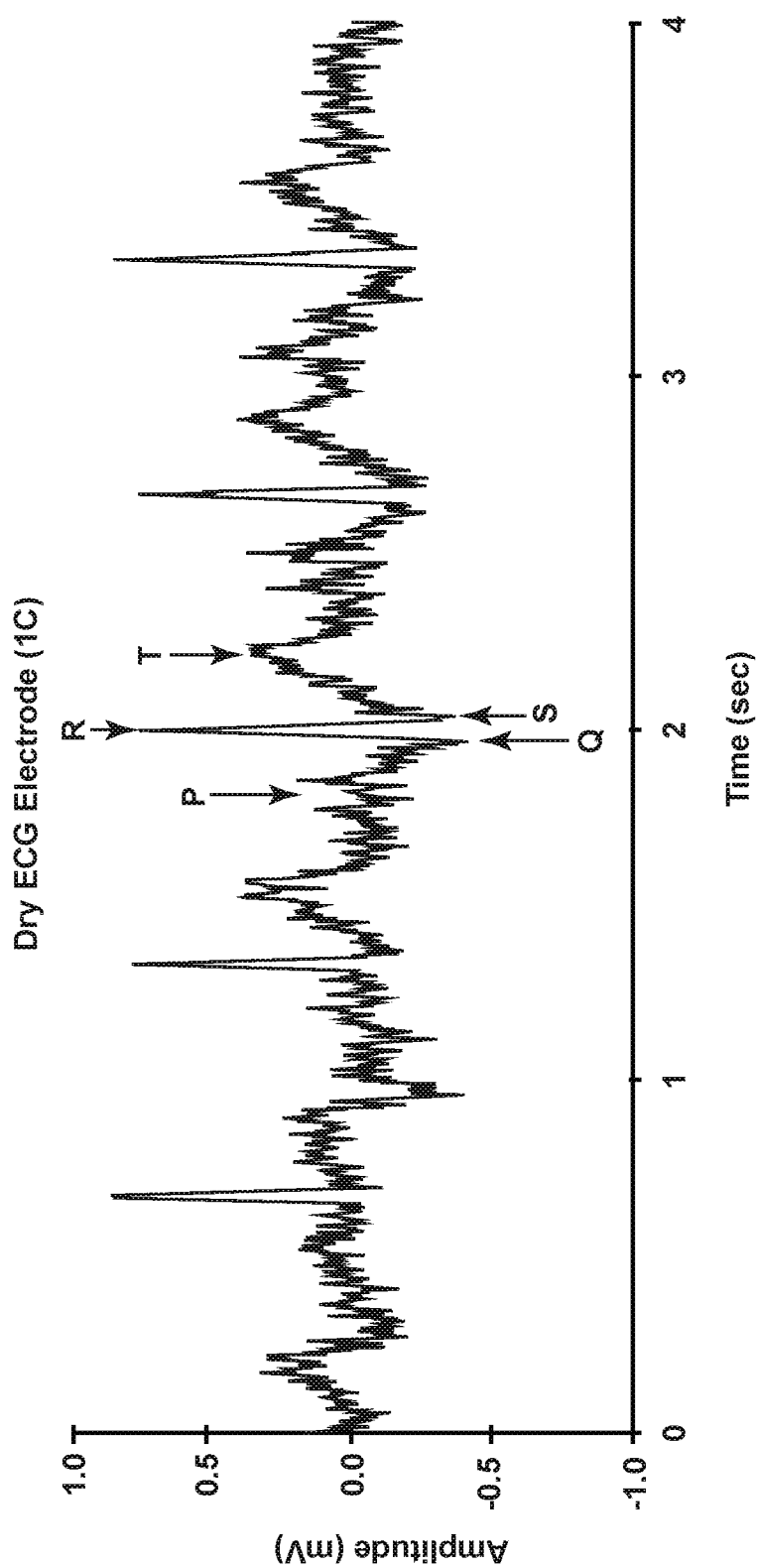
FIG. 5D shows ECG signal measurements for a dry third electrode while the body is in motion.

The signal quality of the ECG signal, obtained using the printed dry ECG electrodes 1A, 1B, 1C, was then compared to that of the wet Ag/AgCl electrode, in the relaxed position (FIG. 4). In the ECG signals, a specific electrical event during the heart activity triggers different waves. In the results obtained, it was possible to identify the typical ECG characteristic wave components, which include the P wave, QRS complex and the T-wave. The QRS complex occurs as the ventricles in the heart depolarize. The P wave and the T-wave occur before and after the QRS complex, respectively. A correlation of 0.85 (FIG. 4(A)), 0.93 (FIG. 4(B)) and 0.97 (FIG. 4(C)) was calculated between the wet Ag/AgCl electrode sensor and the dry ECG electrodes 1A, 1B, and 1C, respectively. The results obtained demonstrated that dry ECG electrode with larger area (1C) has a better correlation and hence a better electrode performance.

The ECG signal quality, while the body is in motion, was then analyzed and compared between the wet Ag/AgCl electrode and the printed dry ECG electrodes 1A, 1B, 1C. The responses of the wet and dry electrodes are shown in FIG. 5. It was observed that ECG signals obtained from the wet Ag/AgCl electrode and the printed dry ECG electrodes (1A and 1B) were less stable and noisier (FIGS. 5(A), (B) and (C)). Therefore, the QRS complexes, P-wave and T-wave could not be observed clearly. The QRS complexes may be used to define and detect the R-R Interval (RRI) length, which is used to calculate the interval between neighboring QRS complexes and can reflect the information of the heart rate. In this test, it was difficult to observe and distinguish the R-peak for the wet Ag/AgCl electrode and the printed dry ECG electrodes (1A and 1B), due to the effect of motion artifacts. However, the response of the printed dry ECG electrode (1C) was better, in terms of identifying the typical ECG characteristic components: the P-wave, QRS complex and the T-wave (FIG. 5(D)). The results obtained demonstrate the capability of the fabricated printed dry electrode ECG sensor (1C) to detect the RRI and perform better than the wet Ag/AgCl sensor electrode and the printed dry electrodes (1A and 1B), while in motion.

SUMMARY

Flexible dry ECG electrodes according to the present disclosure may be fabricated by integrating MWCNT/PDMS composite conductive polymers with a screen printing process. In the example discussed above, three different sizes of electrodes (1A, 1B, 1C) were fabricated by screen printing Ag ink on flexible PET substrate 6 (FIG. 10) and MWCNT/PDMS was then bar coated on the printed Ag 4 to form composite outer layer 2. The capability of the flexible dry ECG electrodes 1A, 1B, 1C for monitoring ECG signals, without the use of any conductive gels or skin preparation, was investigated in both the relaxed sitting position and while the body is in motion. The electrode performance was analyzed by comparing the responses of the fabricated electrodes 1A, 1B, 1C to that of a wet Ag/AgCl electrode. It was observed that the printed dry ECG electrode (1C), with the largest electrode-skin interface area, had a better electrode performance in terms of peak-to-peak signal intensity and correlation when compared to the wet Ag/AgCl electrode, in the relaxed position. Moreover, the typical ECG characteristic components were better distinguishable in the printed dry electrode (1C) when compared to the wet Ag/AgCl electrode and the printed dry electrodes (1A and 1B), while in motion.

It is to be understood that variations and modifications can be made on the aforementioned structure without departing from the concepts of the present invention, and further it is to be understood that such concepts are intended to be covered by the following claims unless these claims by their language expressly state otherwise. Specifically, the layers 2, 4, and 6 are not necessarily limited to the specific materials described herein. For example, spherical or approximately spherical carbon nanoparticles and/or carbon nanotubes (CNTs) could be utilized instead of (or in combination with) WMCNTs. Other suitable polymers could be utilized instead of PDMS. Also, the composite layer 2 could be formed using processes other than bar coating. Examples includes inkjet, screen, gravure, or flexo printing. Similarly, the conductive layer 4 may be formed using various conductive materials/inks (e.g. silver, gold, copper, etc.) that are applied using additive deposition processes such as inkjet, screen, gravure, and flexo printing.

The flexible substrate 6 could comprise other suitable materials such as polyethylene napthalate (PEN), polyimide (Kapton®), or thermoplastic polyurethanes (TPUS). Although polymer materials are preferred for flexible substrate 6, virtually any non-conductive material having sufficient flexibility to conform to a body part may be utilized. Furthermore, the weight percentage of MWCNTs of the composite layer 2 may be about 8% as described above, or other weight percentages (e.g. at least about 2%, 4%, 6%, or ranges of about 6%-10%, 4%-20%, or 1%-50%) may also be utilized. In general, any weight % of CNTs or MWCNTs providing sufficient electrical conductivity to permit accurate ECG readings may be utilized. Still further, other types of conductive particles (e.g. carbon flakes) may also be utilized in the composite layer 2.

The thickness of composite layer 2, conductive layer 4, and flexible substrate 6 are not limited to a specific range. However, substrate 6 may have a thickness of about 50 μm to about 1000 μm, conductive layer 4 may have a thickness of about 300 nm to about 60 μm, and composite layer 2 may have a thickness of about 500 nm to about 1000 μm.

The invention claimed is:

1. A method of fabricating a dry electrode, the method comprising:
   printing conductive ink onto a non-conductive flexible polymer substrate to form a conductive layer having an upper surface;
   forming a layer of electrically conductive composite material on the conductive layer by coating at least a substantial majority of the upper surface of the conductive layer with an electrically conductive composite material comprising carbon nanoparticles and a polymer material to form a dry electrode having sufficient flexibility to conform to skin of a patient when the layer of electrically conductive composite material is brought into contact with skin of a patient.

2. The method of claim 1, wherein:
the polymer material of the composite material comprises polydimethylsiloxane.

3. The method of claim 1, wherein:
the non-conductive flexible polymer substrate comprises a material selected from the group consisting of polyethylene terephthalate (PET), polyethylene napthalate (PEN), polyimide (Kapton®), and thermoplastic polyurethane (TPUS).

4. The method of claim 1, wherein:
the carbon nanoparticles comprise multiwall carbon nanotubes (MWCNTs), and the conductive ink comprises silver.

5. The method of claim 1, wherein:
the carbon nanoparticles comprise carbon nanotubes (CNTs).

6. The method of claim 4, wherein:
the composite material comprises at least 4% MWCNTs.

7. The method of claim 6, wherein:
the weight percentage of MWCNTs of the composite material is at least 8%.

8. The method of claim 1, wherein:
the non-conductive flexible substrate has a substantially uniform thickness of about 50 μm to about 1000 μm.

9. The method of claim 1, wherein:
the conductive layer has a thickness of about 300 nm to about 60 μm.

10. The method of claim 1, wherein:
the composite material layer has a thickness of about 500 nm to about 1000 μm.

11. The method of claim 1, wherein:
the electrode has a circular perimeter having a diameter of about 16 mm.

12. A method of fabricating a flexible dry electrode, the method comprising:
printing conductive ink onto an upper surface of an electrically non-conductive flexible polymer substrate to form a flexible conductive layer having an upper surface and substantially uniform thickness covering substantially the entire upper surface of the flexible polymer substrate, wherein the flexible polymer substrate comprises polyethylene terephthalate (PET) having substantially uniform thickness of 50 μm to 1000 μm;
coating substantially the entire upper surface of the conductive layer with an electrically conductive composite material comprising carbon nanoparticles and a polymer material to form a layer of electrically conductive composite material having substantially uniform thickness and a flexible dry electrode surface, wherein the entirety of the flexible dry electrode surface of the layer of composite material is exposed, whereby the entire upper dry electrode surface can be brought into contact with skin of a patient by flexing the dry electrode to conform to a body part to form an electrically conductive pathway from the skin to the electrically conductive composite material without positioning conductive material between the flexible dry electrode surface and skin of a patient.

* * * * *